(12) United States Patent
Brattesani et al.

(10) Patent No.: US 6,814,085 B2
(45) Date of Patent: Nov. 9, 2004

(54) DENTAL FLOSS WITH USAGE IDENTIFICATION CAPABILITY

(76) Inventors: Steven J. Brattesani, 3309 Fillmore St., San Francisco, CA (US) 94123; Dean Swift, 66 Kingsdale Ave., Toronto (CA), M2N 3W4; Peter Wollwage, Auf Berg 113, Mauren (LI), FL 9493

( * ) Notice: Subject to any disclaimer, the term of this patent is extended or adjusted under 35 U.S.C. 154(b) by 200 days.

(21) Appl. No.: 10/033,734

(22) Filed: Dec. 28, 2001

(65) Prior Publication Data

US 2002/0144705 A1 Oct. 10, 2002

Related U.S. Application Data

(60) Provisional application No. 60/259,144, filed on Dec. 29, 2000.

(51) Int. Cl.⁷ .............................................. A61C 15/00
(52) U.S. Cl. ................................................... 132/321
(58) Field of Search ........................ 132/321, 329, 132/322; 433/70

(56) References Cited

U.S. PATENT DOCUMENTS

| | | | |
|---|---|---|---|
| 4,162,688 A | 7/1979 | Tarrson et al. ............... 132/92 |
| 4,986,288 A * | 1/1991 | Kent et al. .................. 132/321 |
| 5,098,711 A | 3/1992 | Hill et al. .................... 424/401 |
| 5,226,434 A | 7/1993 | Britton et al. ............... 132/321 |
| 5,357,989 A | 10/1994 | Gathani | |
| 5,518,012 A | 5/1996 | Dolan et al. | |
| 5,732,721 A * | 3/1998 | Pelok .......................... 132/321 |
| 5,875,799 A | 3/1999 | Petrus ......................... 132/323 |
| 5,906,834 A * | 5/1999 | Tseng .......................... 424/486 |
| 5,941,256 A * | 8/1999 | Guay et al. .................. 132/321 |
| 2002/0006385 A1 * | 1/2002 | Tsuchiya ...................... 424/49 |

FOREIGN PATENT DOCUMENTS

| | | | | |
|---|---|---|---|---|
| EP | 0 335 466 A2 | 10/1989 | | |
| GB | 2250817 A * | 6/1992 | ........... A61C/15/02 |
| WO | WO 99/29257 | 6/1999 | | |
| WO | WO 00/12024 | 9/2000 | | |

* cited by examiner

Primary Examiner—Todd E. Manahan
(74) Attorney, Agent, or Firm—Workman Nydegger

(57) ABSTRACT

A colored dental floss that changes color when passed between the teeth. The dental floss is coated or impregnated with one or more agents that facilitate the color change by mechanically rubbing the floss against the oral hard tissue or by chemical reaction or both. In addition, the dental floss can be impregnated or coated with an agent that indicates the present of bacterial, disease, virus, infection or the like. Furthermore, the dental floss can be coated or impregnated with a medicament or anti-microbial agent for treat or prevention of disease and the like.

43 Claims, 1 Drawing Sheet

DENTAL FLOSS WITH USAGE IDENTIFICATION CAPABILITY

CROSS-REFERENCE TO RELATED APPLICATIONS

This application claims priority from U.S. provisional application Ser. No. 60/259,144 filed on Dec. 29, 2000, incorporated herein by reference.

STATEMENT REGARDING FEDERALLY SPONSORED RESEARCH OR DEVELOPMENT

Not Applicable

REFERENCE TO A COMPUTER PROGRAM APPENDIX

Not Applicable

BACKGROUND OF THE INVENTION

1. Field of the Invention

The present invention pertains generally to dental floss, and more particularly to dental floss that is coated or impregnated with one or more agents to facilitate identification of usage and/or identification of the presence of a virus, disease or infection, and/or one or more medicaments for treatment or preventive care.

2. Description of the Background Art

Dental floss is a well known tool for cleaning between teeth, and its use is almost universally recommended by dental care professionals. However, dental floss is often misused or used without paying attention to which portions have already been used. Therefore, it is common for a portion of the floss that has already been used to be passed between different teeth. Unfortunately, such "misuse" can lead to the spread of caries and periodontal diseases. Clinical studies show that caries and periodontal diseases are readily communicable and that within the mouth bacterial contamination can be transmitted from unhealthy sites to healthy sites, allowing periodontal disease to spread. Therefore, there is a need for a dental floss material that provides a visual indication to the user of which portion of the floss has already been used. The present invention satisfies that need, as well as others, and overcomes numerous problems associated with conventional dental floss.

BRIEF SUMMARY OF THE INVENTION

The present invention comprises various dental floss configurations that can show areas of prior use of the dental floss, that can be used for diagnostic purposes, and/or that can be used for treatment purposes.

In accordance with one aspect of the invention, the dental floss changes color when passed between the teeth to indicate that the portion of the dental floss where the color change occurred has been previously used. In this way, the user knows not to pass that same portion of dental floss through his or her teeth so as to avoid transmission of bacterial between teeth. In this embodiment, the dental floss is coated or impregnated with one or more agents that facilitate the color change by mechanically rubbing the floss against the oral hard tissue or by chemical reaction or both. The color change could be light sensitive, phosphorescent or any other change that is visible. Additionally, the color change agent can be, for example, sensitive to friction or chemical reaction alone, or in combination with activation heat (e.g., a temperature range present in the mouth).

According to another aspect of the invention, the dental floss can be coated or impregnated with a medicament or anti-microbial agent for treat or prevention of bacteria, disease, virus, infection or the like. An example would be to coat or impregnate the dental floss with fluoride.

According to still another aspect of the invention, the dental floss can be impregnated or coated with an agent that indicates the present of bacteria, disease, virus, infection or the like. The diagnostic agent can be, for example, sensitive to enzyme presence, mole molecules, or the like, either alone or in combination with activation heat (e.g., a temperature range present in the mouth). The presence of bacteria, disease, infection or the like could then be detected by exposing the dental floss to light (assuming a light sensitive agent is used), by culturing the dental floss, by use of chemical reagents, and other means.

Any combination of the foregoing can be incorporated into the dental floss, along with flavoring or odor enhancing agents (e.g., scented dental floss) if desired.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DETAILED DESCRIPTION OF THE INVENTION

Figure 1:
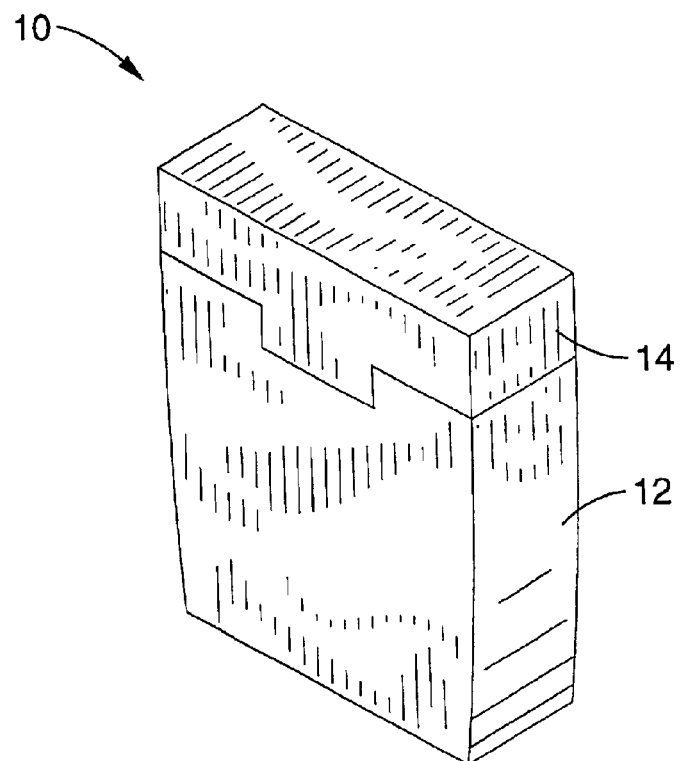
FIG. 1 is a perspective view of an exemplary, non-limiting dental floss assembly employing dental floss according to the present invention.
Figure 2:
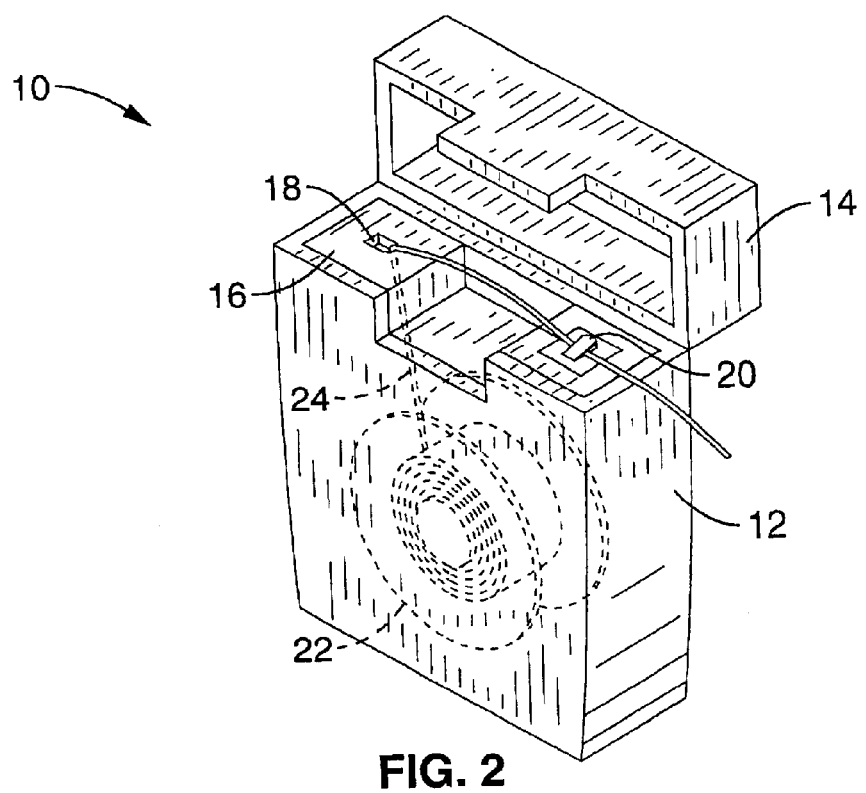
FIG. 2 is a perspective view of an exemplary, non-limiting dental floss assembly of FIG. 1 with the lid opened and the internal components shown in phantom.

Referring to FIG. 1 and FIG. 2, an exemplary, non-limiting dental floss assembly is shown and generally designated 10. FIG. 1 and FIG. 2 show that the dental floss assembly 10 can include a housing 12 and a lid 14. Preferably, the lid 14 is hingedly attached to the housing 12, but it can be attached by any other means well known in the art. Moreover, it can be appreciated that the lid 14 need not be included.

FIG. 2 shows that the housing 12 can include an upper cap 16. As shown, the upper cap 16 can be formed with an opening 18 through which dental floss, described in detail below, is routed from within the housing 12. FIG. 2 further shows that the upper cap 16 can include a cutting mechanism 20 disposed thereon opposite the opening 18. It is to be understood that the cutting mechanism 20 can be a simple, raised metal tab, as shown, or any other such device well known in the art.

As shown in FIG. 2, a spool 22, shown in phantom, is rotatably disposed within the housing 12. A predetermined length of dental floss 24 is wound around the spool 22 and the end of the dental floss 24 is threaded through the opening 18 in the upper cap 16. It is to be understood that a user can pull the end of the dental floss 24 and unwind it from the spool 22. When a desired amount of dental floss 24 is unwound from the spool 22, the user can draw the dental floss 24 laterally across the cutting mechanism 20 in order to cut off the dental floss 24 so that it can easily be used.

In a preferred embodiment, the dental floss 24 is standard dental floss and is made, e.g., from nylon, rayon, etc. However, it can be made from any other material well known in the art. In accordance with the present invention, the dental floss 24 is treated so that it changes color when passed between the teeth during use. It can be appreciated that the color change can simply involve the dental floss 24 glowing in the dark after passed between a user's teeth.

For example, in one embodiment, the dental floss 24 can change color when it is subjected to friction, e.g., when it rubs against hard oral tissue when passed between the teeth. In this embodiment, the dental floss 24 can be coated or impregnated with a conventional coloring material that rubs off during normal use.

In another embodiment, the dental floss 24 changes color when exposed to saliva in the range of in-vivo temperatures. Preferably, the coloring agent applied to the dental floss 24 is reactive to changes in pH which occurs when the dental floss 24 is in the presence of saliva. The range of reactivity that causes a color change is preferably in the range of range of pH 5.0 to pH 9.0.

In still another embodiment, the floss changes color when subjected to friction in the presence of saliva in the range of in-vivo temperatures. Preferably, the pH range that renders the floss reactive to color change is on the order of pH 5.0 to pH 9.0. In this embodiment, simply rubbing the dental floss 24 will not cause a color change, i.e., friction must be combined with the presence of saliva in the specified pH range.

In all of the foregoing embodiments, the dental floss 24 will change color to indicate when the floss has passed between teeth. In this way, a user can easily discern which portion of the dental floss 24 has already been used and avoid re-using the used dental floss 24 to avoid the complications described above. It is to be appreciated that the dental floss 24 is treated so that the coloring agent will not remain on the teeth or tissue. Additionally, the dental floss 24 can be scented or flavored with nearly any appealing scent or flavor well known in the art.

In another embodiment of the present invention, the dental floss 24 can be treated with medication that can be delivered to the area of the user's mouth that is being flossed. For example, the dental floss 24 can be made therapeutic with the addition of anti-microbial agents bacterial materials such as NaF (Sodium Fluoride), CHG (Chlorhexidine digluconate), CHA (Chlorhexidine acetate), or the like. Such agents can be added by coating or impregnating the dental floss 24 with the agent. Quite surprisingly, this formulation increases the strength of the dental floss 24, decreases the ability to fray, slides easier between tight contacts of the dentition, and creates a lubricating effect. In this aspect of the present invention, the dental floss 24 can be scented or flavored with nearly any appealing scent or flavor well known in the art. Thus, an aversion to applying an unappealing medication to the mouth via the dental floss 24 can be overcome.

In accordance with a still further embodiment of the invention, the dental floss 24 can be coated or impregnated with one or more virus or disease condition indicators. For example, in one exemplary, non-limiting embodiment, the dental floss 24 is coated or impregnated with a disease indicator, e.g., Periocheck™ available from Rotadent. Also, in one exemplary, non-limiting embodiment, the dental floss 24 can be coated or impregnated with an oral cancer detection agent, e.g., Oral CDX™ available from Shein Corporation. Furthermore, the dental floss 24 can be impregnated or coated with 0 to 100% fluorescein sodium which is a fluoroscopic material used as a plaque indicator, and which is described in U.S. Pat. No. 3,309,274 incorporated herein by reference.

It is to be understood that in this aspect of the present invention, the dental floss 24 can be treated to detect the presence of enzymes that are indicative of medical conditions, e.g., detecting enzymes that are indicative of diabetes. This particular dental floss 24 can change colors when the enzymes in question are detected. It can be appreciated that this particular dental floss 24 can be reactive to the enzymes only or it can be reactive when exposed to the enzymes in the range of in-vivo temperatures.

Also, the dental floss 24 can be treated so that when properly used, i.e., passed between to adjacent teeth, bacteria stick thereto. Thereafter, the dental floss 24 can be placed under a special light in order to detect the bacteria attached to the dental floss 24.

Those skilled in the art will appreciate that the present invention encompasses dental floss with means for providing visual indication of a portion that has been passed between the teeth, means for providing indication of the presence of a virus, infection, bacteria, disease, plaque or other condition, means for administering a medicament or anti-microbial agent, means for strengthening the floss, and means for making the floss slipperier and easier to pass between the teeth without slipping over bacteria present. Any one or combination of these can be employed in the inventive floss. Conventional dental floss is coated or impregnated with one or more materials that provide one or more of the foregoing indicating or treatment characteristics.

With the foregoing in mind, the following formulation represents the preferred embodiment of the material used to coat or impregnate the floss:

| | |
|---|---|
| $K_2CO_3$ | 0–5% |
| $Na_2CO_3$ | 0–5% |
| Glycerol | 0–5% |
| $H_2O$ | 30–60% |
| Ethanol | 30–60% |
| Flavorings | 0–2% |
| CHG/CHA | 0–.5% |
| NaF | 0–.5% |
| Indicator dyes | 0.1–3.0% |
| Soluble polymers | 10–40% |
| Triethanol amine | 0–5% | wherein the indicator dyes are selected from the group of indicator dyes consisting of thymol blue, Bromthymolphthalein and other non-toxic pH indicators as well as specific aerobic and anaerobic bacteria, virus and disease condition indicators; and wherein the soluble polymers are selected from the group of soluble polymers consisting of cellulose and polyethylene oxide pyrlidone. The material is mixed in a solution, and then, the dental floss is coated or impregnated and dried in any conventional manner.

Although the description above contains many specificities, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. In dental floss, the improvement comprising:
coating or impregnating said dental floss with a colored material to yield a dental floss that is colored prior to use and that changes color though removal of said colored material from said colored dental floss when said colored dental floss is passed between the teeth of a user in order to indicate which portion or said dental floss has been used.

2. In dental floss, the improvement comprising;
coating or impregnating said dental floss with a color-changing material that changes color in response to changes in pH throughout a pH range of 5.0 to 9.0 when said dental floss is exposed to saliva and which does not remain on a user's teeth.

3. In dental floss, the improvement comprising:
coating or impregnating said dental floss with an indicator dye comprising at least one of thymol blue or bromthymolphthualein and which does not remain on a user's teeth.

4. In dental floss, the improvement comprising:
coating or impregnating said dental floss with a color-changing material that changes color when said dental floss contacts particular enzymes in a mouth as a result of a chemical reaction between said color-changing material and the particular enzymes.

5. In dental floss, the improvement comprising:
coating or impregnating said dental floss with a color-changing material that changes color when said dental floss contacts particular enzymes in a mouth within an in vivo temperature range.

6. In dental floss, the improvement comprising:
coating or impregnating said dental floss with a disease indicating agent that indicates and specifically identifies the presence of one or more of a virus, disease, infection, bacteria, or plaque,
said disease indicating agent characterized by at least one of the following:
(i) being sensitive to enzyme presence;
(ii) being a fluoroscopic material;
(iii) being an oral cancer detecting; or
(iv) being a diabetes detecting agent.

7. In dental floss comprising nylon or rayon, the improvement comprising:
directly coating or impregnating said dental floss comprising nylon or rayon with a medicament or anti-microbial material mixed within a composition comprising water, ethanol, and one or more water-soluble polymers;
drying said dental floss; and
winding said coated or impregnated dental floss onto a spool for storage and later use.

8. A dental hygiene material, comprising:
dental floss; and
a coloring material coating said dental floss or impregnated in said dental floss so that said dental floss is colored prior to use and so that said dental floss changes color when passed between two adjacent teeth so as to remove at least a portion of the coloring material from the portion of the dental floss passed between adjacent teeth and indicate which portion of said dental floss has been used.

9. A dental hygiene material, comprising:
dental floss; and
color-changing material coating said dental floss or impregnated in said dental floss that changes color in response to changes in pH throughout a pH range of 5.0 to 9.0 when said dental floss is exposed to saliva and which does not remain on a user's teeth.

10. A dental hygiene material, comprising:
dental floss; and
an indicator dye comprising at least one of thymol blue or bromthymolphthalein and which does not remain on a user's teeth.

11. A dental hygiene material, comprising:
dental floss; and
a color-changing material coating said dental floss or impregnated in said dental floss that changes color when said dental floss contacts particular enzymes in a mouth as a result of a chemical reaction between said color-changing material and the particular enzymes.

12. A dental hygiene material, comprising:
dental floss; and
a color-changing material coating said dental floss or impregnated in said dental floss that changes color when said dental floss contacts particular enzymes in a mouth within an in vivo temperature range.

13. A dental hygiene material, comprising:
dental floss; and
a disease indicating agent coating said dental floss or impregnated in said dental floss that is capable of indicating and specifically identifying the presence of one or more of a virus, disease, infection, bacteria, or plaque,
said disease indicating agent characterized by at least one of the following:
(i) being sensitive to enzyme presence;
(ii) being a fluoroscopic material;
(iii) being an oral cancer detecting agent; or
(iv) being a diabetes detecting agent.

14. A dental hygiene material, comprising:
dental floss comprising nylon or rayon wound onto a spool for storage and later use; and
a medicament or anti-microbial material directly coating said dental floss or impregnated in said dental floss and that was applied to said dental floss mixed in a composition comprising water, ethanol and one or more water-soluble polymers.

15. A method for identifying whether dental floss has been passed between the teeth of a user, comprising:
providing a colored dental floss coated or impregnated with a colored material so that said dental floss is colored prior to use; and
passing a portion of said colored dental floss between adjacent teeth of the user in order to remove at least some of said colored material from the portion of said dental floss that is passed between the adjacent teeth and indicate which portion of said dental floss has been used.

16. A method for identifying whether dental floss has been passed between the teeth of a user, comprising:
  providing dental floss coated or impregnated with a color-changing material that changes color in response to changes in pH throughout a pH range of 5.0 to 9.0 when said dental floss is exposed to saliva; and
  passing a portion of said dental floss between adjacent teeth of the user in order for said portion of said dental floss to change color without said color-changing material remaining on the user's teeth.

17. A method for identifying whether dental floss has been passed between the teeth of a user, comprising:
  providing dental floss coated or impregnated with an indicator dye comprising at least one thymol blue or bromthymolphthalein; and
  passing a portion of said dental floss between adjacent teeth of the user in order for said portion of said dental floss to change color without said indicator dye remaining on the user's teeth.

18. A method for identifying whether dental floss has been passed between the teeth of a user, comprising:
  providing dental floss coated or impregnated with a color-changing material that changes color when said dental floss contacts particular enzymes in a mouth as a result of a chemical reaction between said color-changing material and the particular enzymes; and
  passing a portion of said dental floss between adjacent teeth of the user.

19. A method for identifying whether dental floss has been passed between the teeth of a user, comprising:
  providing dental floss coated or impregnated with a color-changing material that changes color when said dental floss contacts particular enzymes in a mouth within an in vivo temperature range; and
  passing a portion of said dental floss between adjacent teeth of the user.

20. A method for identifying the presence of virus, disease, infection, bacterial or plaque between tho teeth of a user, comprising:
  providing dental floss coated or impregnated with a disease indicating agent that indicates and specifically identifies the presence of one or more of a virus, disease, infection, bacteria, or plaque,
    said disease indicating agent characterized by at least one of the following:
      (i) being sensitive to enzyme presence;
      (ii) being a fluoroscopic material;
      (iii) being an oral cancer detecting agent; or
      (iv) being a diabetes detecting agent; and
  passing a portion of said dental floss between adjacent teeth of the user.

21. A method for administering a medicament or anti-microbial agent between the teeth of a user, comprising:
  providing dental floss that comprises nylon or rayon, that is directly coated or impregnated with a medicament or anti-microbial material that was applied to said dental floss mixed in a composition comprising water, ethanol and one or more water-soluble polymers, and that has been wound onto a spool after being coated or impregnated with said medicament or anti-microbial material for storage and later use; and
  passing a portion of said dental floss between adjacent teeth of the user.

22. Dental floss coated or impregnated with a material consisting essentially of:
  0 to 5% $K_2CO_3$, 0 to 5%, $Na_2CO_3$, 0–5% glycerol, 30 to 60% $H_2O$, 30 to 60% ethanol, 0 to 2% flavorings, 0 to 0.5% CHG/CHA, 0 to 0.5% NaF, 0.1 to 3.0% indicator dyes, 10 to 40% water soluble polymers, and 0 to 5% Triethanol amine;
  wherein the indicator dyes are selected from the group of indicator dyes consisting of thymol blue, bromthymolphthalein and specific acrobic and anaerobic bacteria, virus and disease condition indicators, and
  wherein the dental floss is subsequently dried after being coated or impregnated with the material.

23. A dental floss assembly, comprising:
  a housing;
  at least one spool of dental floss disposed within said housing; and
  a colored or color-changing material coating or impregnated within said dental floss that causes said dental floss to change color when said dental floss is passed between the teeth of a user in order to indicate which portion of said dental floss has been used, but which does not remain on the teeth, as a result of at least one of the following:
    (i) through removal of said colored or color-changing material when said dental floss in used to floss teeth,
    (ii) in response to changes in pH throughout a pH range of 5.0 to 9.0,
    (iii) because said colored or color-changing material is an indicator dye comprising at least one of thymol blue or bromthymolphthalein, or
    (iv) as a result of a chemical reaction between said colored or color-changing material and particular enzymes found in the mouth of a user.

24. A dental floss assembly as recited in claim 23:
  wherein said dental floss changes color when subjected to friction.

25. A dental floss assembly as recited in claim 23:
  wherein said dental floss changes color when said dental floss is subjected to friction in the presence of saliva.

26. A dental floss assembly as recited in claim 24:
  wherein said dental floss changes color when said dental floss is subjected to friction in the presence of saliva within an in viva temperature range.

27. A dental floss assembly as recited in claim 23:
  wherein said dental floss changes color when said dental floss contacts particular enzymes.

28. A dental floss assembly as recited in claim 27:
  wherein said dental floss changes color when said dental floss contacts particular enzymes within an in vivo temperature range.

29. A dental floss assembly, comprising:
  a housing;
  at least one spool of dental floss disposed within said housing for storage and later use, said dental floss comprising nylon or rayon; and
  a medicament directly coating or impregnating said dental floss and that was applied to said dental floss mixed in a composition comprising water, ethanol and one or more water-soluble polymers.

30. A dental floss assembly as recited in claim 29:
  wherein said medicament comprises an anti-microbial agent.

31. A dental floss assembly as recited in claim 29:

wherein said medicament comprises sodium fluoride (NaF).

32. A dental floss assembly as recited in claim 29:

wherein said medicament comprises chlorhexidine digluconate (CHG).

33. A dental floss assembly as recited in claim 29:

wherein said medicament comprises chlorhexidine acetate (CHA).

34. A dental floss assembly as recited in claim 29:

wherein said dental floss is scented.

35. A dental floss assembly as recited in claim 29:

wherein said dental floss is flavored.

36. A dental floss assembly, comprising:

a housing;

at least one spool of dental floss disposed within said housing; and a disease indicating agent coating or impregnating said dental floss that indicates and specifically identifies the presence of a particular oral disease if present in a user's mouth, said disease indicating agent characterized by at least one of the following:

(i) being sensitive to enzyme presence;
(ii) being a fluoroscopic material;
(iii) being an oral cancer detecting agent; or
(iv) being a diabetes detecting agent.

37. A dental floss assembly as recited in claim 36:

wherein said disease indicating agent is an oral cancer detecting agent.

38. A dental floss assembly as recited in claim 36:

wherein said disease indicating agent comprises a plaque indicator.

39. A dental floss assembly as recited in claim 38:

wherein said plaque indicator comprises fluorescein sodium.

40. A dental floss assembly as recited in claim 38:

wherein said plaque indicator comprises an enzyme detector.

41. A dental floss assembly as recited in claim 36:

wherein said disease indicating agent detects enzymes that are indicative of diabetes.

42. A dental floss assembly as recited in claim 36:

wherein said dental floss is scented.

43. A dental floss assembly as recited in claim 36:

wherein said dental floss is flavored.

\* \* \* \* \*